United States Patent
Okabe et al.

(10) Patent No.: US 10,506,913 B2
(45) Date of Patent: Dec. 17, 2019

(54) APPARATUS OPERATION DEVICE, APPARATUS OPERATION METHOD, AND ELECTRONIC APPARATUS SYSTEM

(71) Applicant: FUJIFILM Corporation, Tokyo (JP)

(72) Inventors: Yuuki Okabe, Tokyo (JP); Mayuko Ikuta, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 116 days.

(21) Appl. No.: 15/891,567

(22) Filed: Feb. 8, 2018

(65) Prior Publication Data
US 2018/0160881 A1 Jun. 14, 2018

Related U.S. Application Data

(63) Continuation of application No. PCT/JP2016/069885, filed on Jul. 5, 2016.

(30) Foreign Application Priority Data

Aug. 28, 2015 (JP) ................. 2015-169057

(51) Int. Cl.
*A61B 1/00* (2006.01)
*G02B 23/24* (2006.01)
*A61B 17/00* (2006.01)

(52) U.S. Cl.
CPC ...... *A61B 1/00006* (2013.01); *A61B 1/00048* (2013.01); *G02B 23/243* (2013.01); *A61B 2017/00216* (2013.01)

(58) Field of Classification Search
CPC . A61B 1/00006; A61B 3/113; A61B 1/00048; A61B 1/00; A61B 2017/00216;
(Continued)

(56) References Cited

U.S. PATENT DOCUMENTS 6,346,929 B1 2/2002 Fukushima et al.
2012/0235064 A1 9/2012 Guez
(Continued)

FOREIGN PATENT DOCUMENTS

EP 2856923 A1 4/2015
JP H08-006708 A 1/1996
(Continued)

OTHER PUBLICATIONS

Extended European Search Report issued by the European Patent Office dated Jul. 19, 2018, which corresponds to EP16841273.2-1124 and is related to U.S. Appl. No. 15/891,567.
(Continued)

*Primary Examiner* — Jared Walker
(74) *Attorney, Agent, or Firm* — Studebaker & Brackett PC (57) ABSTRACT

In an endoscope system according to an embodiment of the present invention, it is not necessary to touch an actual keyboard, mouse, or button to operate an endoscope apparatus, and thus it is not necessary to shift an instrument from one hand to the other hand or peel of/put on gloves in a medical setting. Accordingly, a necessary operation can be easily performed by using a line of sight and a gesture. In addition, it is not necessary to provide a keyboard, mouse, or button for operating the endoscope apparatus, and restrictions on the arrangement of the apparatus can be reduced. Furthermore, virtual objects corresponding to an apparatus to be operated and operation details are displayed in a pseudo manner, and thus the virtual object on which an operation is to be performed can be easily determined.

23 Claims, 10 Drawing Sheets

(58) Field of Classification Search
CPC ............. G06F 3/04842; G06F 3/04845; G06F 3/0304; G06F 3/017; G06F 3/0425; G06F 3/013; G02B 23/243; G02B 23/24
USPC .......................................................... 348/65
See application file for complete search history.

(56) References Cited

U.S. PATENT DOCUMENTS

| | | | |
|---|---|---|---|
| 2014/0368432 A1* | 12/2014 | Zhang | G06F 3/013 345/158 |
| 2015/0287243 A1 | 10/2015 | Itai | |
| 2016/0004321 A1* | 1/2016 | Takada | G02B 27/01 345/156 |
| 2016/0089980 A1* | 3/2016 | Kurahashi | G06F 3/013 345/156 |
| 2016/0170485 A1 | 6/2016 | Naruse | |

FOREIGN PATENT DOCUMENTS

| | | |
|---|---|---|
| JP | H08-206083 A | 8/1996 |
| JP | H08-336497 A | 12/1996 |
| JP | 2001-070293 A | 3/2001 |
| JP | 2014-113209 A | 6/2014 |
| JP | 2014-516595 A | 7/2014 |
| JP | 2014-149640 A | 8/2014 |
| JP | 2014-218199 A | 11/2014 |
| JP | 2015-093147 A | 5/2015 |
| WO | 2014/103238 A1 | 7/2014 |
| WO | 2015/143067 A1 | 9/2015 |

OTHER PUBLICATIONS

International Search Report; issued in PCT/JP2016/069885; dated Sep. 27, 2016.
International Preliminary Report on Patentability; issued in PCT/JP2016/069885; dated Oct. 4, 2017.
An Office Action mailed by the Japanese Patent Office dated Feb. 25, 2019, which corresponds to Japanese Patent Application No. 2017-537618 and is related to U.S. Appl. No. 15/891,567.

\* cited by examiner

APPARATUS OPERATION DEVICE, APPARATUS OPERATION METHOD, AND ELECTRONIC APPARATUS SYSTEM

CROSS-REFERENCE TO RELATED APPLICATIONS

This application is a Continuation of PCT International Application No. PCT/JP2016/069885 filed on Jul. 5, 2016, which claims priority under 35 U.S.C. § 119(a) to Japanese Patent Application No. 2015-169057 filed Aug. 28, 2015. Each of the above application(s) is hereby expressly incorporated by reference, in its entirety, into the present application.

BACKGROUND OF THE INVENTION

1. Field of the Invention

The present invention relates to an apparatus operation device, an apparatus operation method, and an electronic apparatus system, and particularly relates to a technique for operating an apparatus by using a line of sight and a gesture of a user.

2. Description of the Related Art

Various types of apparatuses are typically operated by a user directly touching an apparatus with his/her hand or foot or operating an operation apparatus or device provided in the apparatus. However, depending on a type or usage situation of an apparatus, restrictions may be imposed on a user's action of operating a main body of the apparatus or a peripheral apparatus, or on the arrangement of the operation apparatus or device. For example, in an operation of a mobile apparatus, such as a smartphone or a game machine, driving of a car, or an operation of a medical apparatus, a user may be unable to freely use both hands while holding or operating the apparatus. As for a medical apparatus, the user may need to peel of/put on gloves or wash hands before/after operating the apparatus, and it may be difficult to smoothly operate the apparatus.

Accordingly, a technique for operating an apparatus by using a line of sight and a gesture in these situations is known (see, for example, JP2014-218199A, JP2014-149640A, and JP2001-070293A). JP2014-218199A describes that a line of sight of a driver is detected to select an image displayed on a windshield of a car and the selection of the image is confirmed by a motion of a hand. JP2014-149640A describes that a target apparatus to be operated, such as an instrument panel switch, is selected by using a line of sight and a gesture, such as a hand gesture, sign, or change in the shape of a hand, of a driver, and then the selected apparatus is operated. JP2001-070293A describes that an operation, such as selection of a command of an X-ray diagnostic apparatus, is performed by using visual point detecting means and noncontact fingertip detecting means.

SUMMARY OF THE INVENTION

However, in the related art described in JP2014-218199A, JP2014-149640A, and JP2001-070293A, it is not easy to perform a necessary operation. For example, in JP2014-218199A and JP2014-149640A, if an operation to be performed is complicated, an action of a user (movement of a line of sight or a gesture) is complicated and troublesome. If a necessary gesture is forgotten, performing a gesture is likely to interfere with driving of a car. In JP2001-070293A, fingertip detecting means that is provided near a hand of an operator is used, but use of an actual instrument or the like for operating an apparatus is likely to restrict the arrangement of the apparatus.

As described above, in the related art, it is difficult to easily perform a necessary operation in an apparatus that is to be operated by using a line of sight and a gesture, and many restrictions are imposed on the arrangement of the apparatus.

The present invention has been made in view of the above-described circumstances, and an object of the present invention is to provide an apparatus operation device, an apparatus operation method, and an electronic apparatus system that enable a necessary operation to be easily performed by using a line of sight and a gesture and that reduce restrictions on the arrangement of an apparatus.

To achieve the above-described object, an apparatus operation device according to a first aspect of the present invention includes a line-of-sight detecting unit that detects a line of sight of a user; a pseudo display unit that displays a virtual object in a pseudo manner; a gesture detecting unit that detects one or more gestures of the user performed on the virtual object that is displayed in a pseudo manner; a determining unit that determines, based on the line of sight that has been detected and the one or more gestures that have been detected, a target apparatus to be operated and operation details for the target apparatus; and a control unit that controls the target apparatus and causes the target apparatus to execute the operation details that have been determined, wherein the line-of-sight detecting unit detects a first point of gaze from an image of the user's eye, and detects a second point of gaze according to a movement of the line of sight, and the determining unit determines, based on the movement of the line of sight between the detected first point of gaze and second point of gaze, the target apparatus and the operation details for the target apparatus.

In the apparatus operation device according to the first aspect, a virtual object is displayed in a pseudo manner and a gesture performed on the virtual object is detected, and thus a necessary operation can be easily performed. In addition, since determination and control are performed based on a line of sight and a gesture performed on a virtual object, it is not necessary to actually provide an instrument or member for operation and it is not necessary to directly touch the instrument or member. Accordingly, restrictions on the arrangement of the apparatus are reduced.

In the first aspect, pseudo display of a virtual object may be performed in accordance with a target apparatus to be operated and operation details. Specifically, for example, an object to be displayed in a pseudo manner and a display mode can be determined by considering conditions, for example, which type of apparatus is used as a target apparatus to be operated, and which process can be executed by the target apparatus.

In the first aspect, a virtual object that is displayed in a pseudo manner may be an object imitating an instrument or member that is actually used for an operation or may be an object unrelated to the instrument or member. The virtual object may have a character, figure, or symbol displayed thereon or may be colored in accordance with a target apparatus to be operated and operation details. Alternatively, the display may be changed in accordance with a gesture that has been detected. A gesture may be performed by using a part of the body, such as a hand or foot. In the first aspect, a single target apparatus to be operated may be used, or one or more apparatuses may be selected from among a plurality of apparatuses, based on a line of sight and a gesture.

Moreover, according to the first aspect, a target apparatus to be operated and operation details are determined based on not only the position of a line of sight (point of gaze) at a certain point of time but also a movement of the line of sight, and thus the target to be operated and the operation details can be appropriately designated.

In an apparatus operation device according to a second aspect, in the first aspect, the determining unit determines, based on the movement of the line of sight that has been detected and a first gesture among the one or more gestures that have been detected, the target apparatus and the operation details, and confirms the determination, based on a second gesture among the one or more gestures that have been detected. The second aspect is for defining a condition for confirming the determination. The second gesture is a gesture for confirming the determination and thus may be simpler than the first gesture.

In an apparatus operation device according to a third aspect, in the second aspect, the virtual object is one of a plurality of virtual objects, the pseudo display unit displays the plurality of virtual objects in a pseudo manner, and the gesture detecting unit detects, as the first gesture, a gesture performed on a first virtual object among the plurality virtual objects, and detects, as the second gesture, a gesture performed on a second virtual object among the plurality of virtual objects. The first and second virtual objects may be simultaneously displayed. Alternatively, the first virtual object may be displayed first, the first gesture may be detected, and then the second virtual object may be displayed.

In an apparatus operation device according to a fourth aspect, in any one of the first to third aspects, the operation details include a function that the control unit causes the target apparatus to execute, and an execution condition for the function. In the fourth aspect, an "execution condition" is a specific value of a condition that needs to be specified to execute a function, for example, a range, an amount, a time, or a level of a process.

In an apparatus operation device according to a fifth aspect, in any one of the first to fourth aspects, the a hand gesture of the user. The fifth aspect defines a specific portion used in a gesture. In the fifth aspect, a gesture of a portion from a wrist to fingertips may be detected.

In an apparatus operation device according to a sixth aspect, in any one of the first to fifth aspects, the line-of-sight detecting unit suspends detection of the line of sight upon detection of the one or more gestures being started by the gesture detecting unit, and starts detection of the line of sight upon detection of the one or more gestures being finished by the gesture detecting unit.

To achieve the above-described object, an apparatus operation method according to an seventh aspect of the present invention is an apparatus operation method for an apparatus operation device including a line-of-sight detecting unit that detects a first point of gaze from an image of the user's eye, and a second point of gaze according to a movement of the line of sight, a pseudo display unit that displays a virtual object in a pseudo manner, and a gesture detecting unit that detects one or more gestures of the user performed on the virtual object that is displayed in a pseudo manner, the apparatus operation method including a determination step of determining, based on the line of sight between the first point of gaze and the second point of gaze that has been detected by the line-of-sight detecting unit and the one or more gestures that have been detected by the gesture detecting unit, a target apparatus to be operated and operation details for the target apparatus; and a control step of controlling the target apparatus and causing the target apparatus to execute the operation details that have been determined. In the apparatus operation method according to the seventh aspect, a necessary operation can be easily performed by using a line of sight and a gesture performed on a virtual object, and restrictions on the arrangement of the apparatus can be reduced, as in the first aspect.

To achieve the above-described object, an electronic apparatus system according to a eighth aspect of the present invention includes the apparatus operation device according to any one of the first to sixth aspects; and an electronic apparatus which is the target apparatus.

In an electronic apparatus system according to a ninth aspect, in the eighth aspect, the electronic apparatus includes an image display unit that displays an image, and the control unit controls the electronic apparatus and causes the electronic apparatus to process the image displayed on the image display unit. According to the ninth aspect, a process for an image obtained by the electronic apparatus can be executed by using a line of sight and a gesture.

In an electronic apparatus system according to an tenth aspect, in the eighth or ninth aspect, the electronic apparatus is a medical apparatus. In a medical apparatus, there are restrictions on the maintenance, actions, usage situations, and so forth. In the electronic apparatus system according to the tenth aspect, a medical apparatus can be easily operated by using a line of sight and a gesture performed on a virtual object, and the arrangement of the apparatus is less restricted.

An apparatus operation device, an apparatus operation method, and an electronic apparatus system according to the present invention enable a necessary operation to be easily performed by using a line of sight and a gesture, and reduce restrictions on the arrangement of an apparatus.

DESCRIPTION OF THE PREFERRED EMBODIMENTS

First Embodiment

Figure 1:
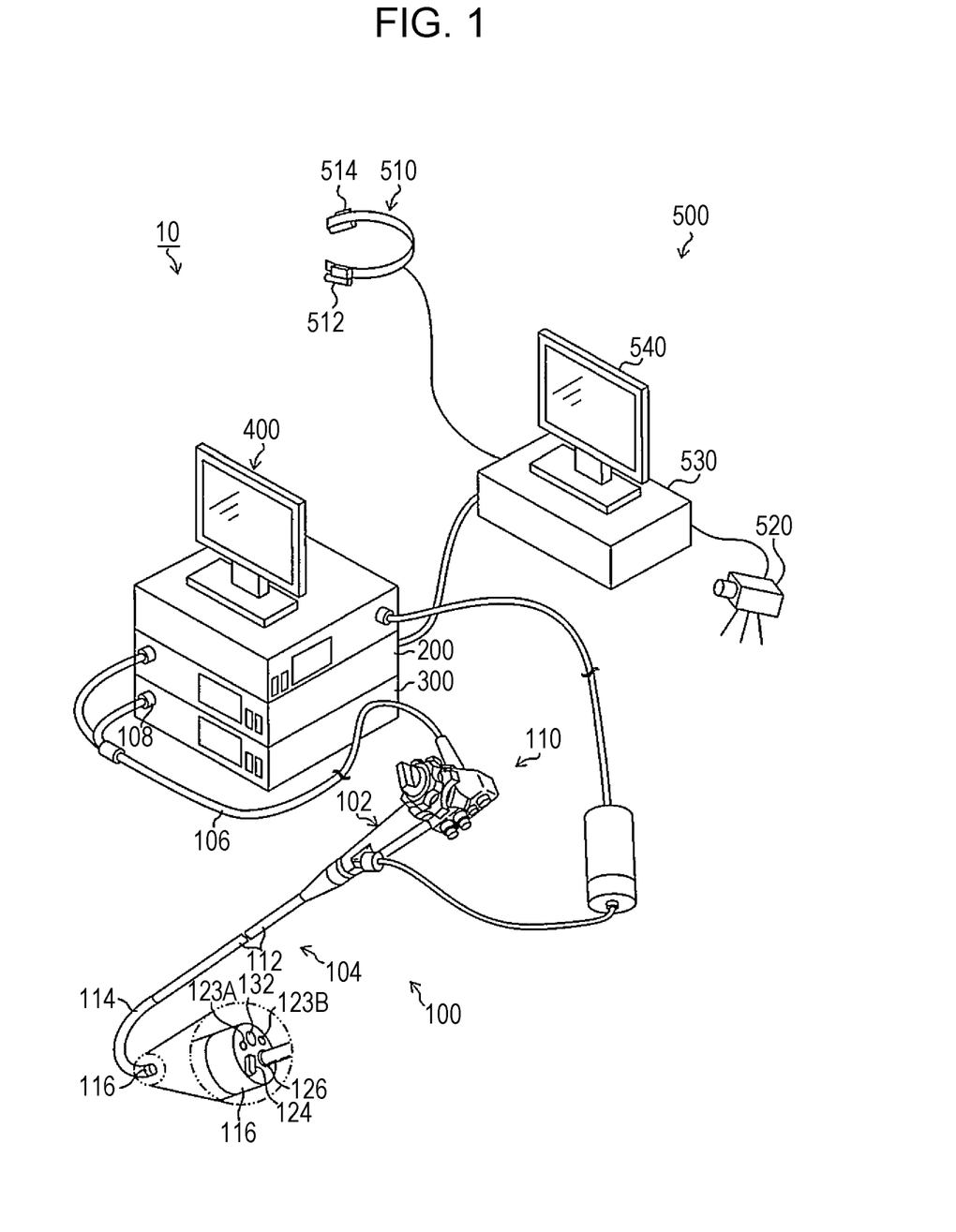
FIG. 1 is a diagram illustrating the overall configuration of an electronic apparatus system according to an embodiment of the present invention.
Figure 2:
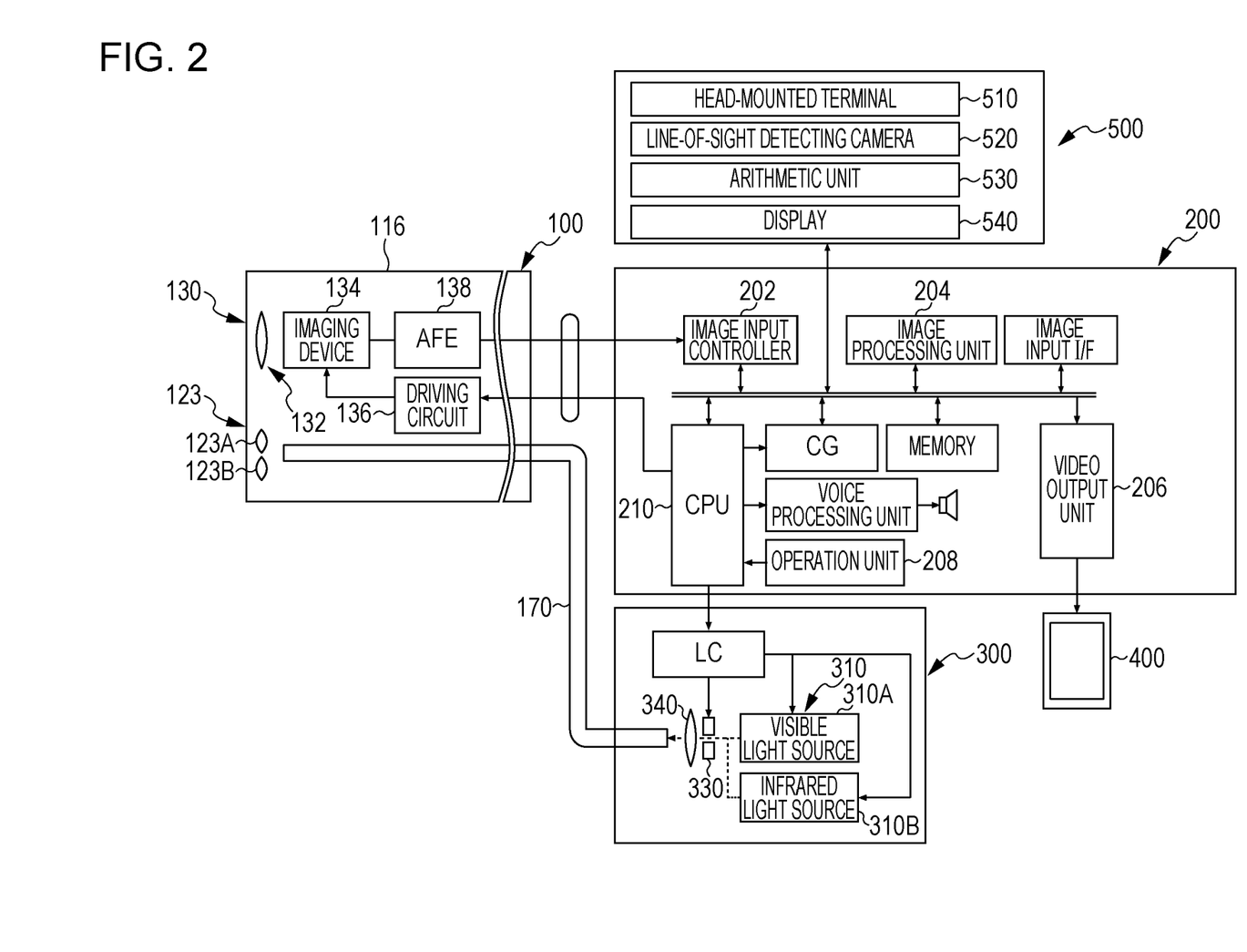
FIG. 2 is a block diagram illustrating the configuration of the electronic apparatus system according to an embodiment of the present invention.

Hereinafter, an embodiment of an apparatus operation device, an apparatus operation method, and an electronic apparatus system according to the present invention will be described with reference to the attached drawings. FIG. 1 is an external view illustrating an endoscope system 10 (an electronic apparatus system) according to a first embodiment. FIG. 2 is a block diagram illustrating the configuration of a main part of the endoscope system 10. As illustrated in FIGS. 1 and 2, the endoscope system 10 includes an endoscope apparatus 100 (an electronic apparatus which is a medical apparatus) formed of an endoscope main body 110, an endoscope processor 200, a light source device 300, and a monitor 400 (an image display unit), and an endoscope operation device 500 (an apparatus operation device).

Configuration of Endoscope Main Body

The endoscope main body 110 includes a handheld operation section 102 and an insertion section 104 that is connected to the handheld operation section 102. An operator operates the handheld operation section 102 while grasping it and inserts the insertion section 104 into a body of a subject to perform observation. The insertion section 104 is constituted by a flexible portion 112, a bending portion 114, and a distal end portion 116, which are arranged in this order from the handheld operation section 102 side. The distal end portion 116 is provided with an imaging optical system 130 (see FIG. 2), an illumination unit 123, a water supply nozzle 124, a forceps port 126, and so forth.

At the time of observation or treatment, an operation of an operation unit 208 (see FIG. 2) enables either or both of visible light and infrared light to be emitted from illumination lenses 123A or 123B of the illumination unit 123. In addition, an operation of the operation unit 208 enables washing water to be ejected from the water supply nozzle 124, so that a lens 132 of the imaging optical system 130 and the illumination lenses 123A and 123B can be washed. The forceps port 126 allows a treatment tool, which is used to extirpate or remove a tumor and which is not illustrated, to be inserted therethrough, and accordingly necessary treatment can be given to a subject by moving the treatment tool forward or backward as appropriate.

As illustrated in FIG. 2, the lens 132 of the imaging optical system 130 is disposed on a distal end surface of the distal end portion 116. An imaging device 134 of a complementary metal-oxide semiconductor (CMOS) type, a driving circuit 136, and an analog front end (AFE) 138 are disposed behind the lens 132, so as to output an image signal. In this embodiment, a description will be given of a case where the imaging device 134 is a CMOS type imaging device, but the imaging device 134 may be of a charge coupled device (CCD) type.

An observation image that has been taken through the lens 132 and so forth is formed on a light reception surface of the imaging device 134, converted into an electric signal, output to the endoscope processor 200 through a signal cable that is not illustrated, and converted into a video signal. Accordingly, the observation image is displayed on the monitor 400, which is connected to the endoscope processor 200.

Display of Observation Image

Figure 3:
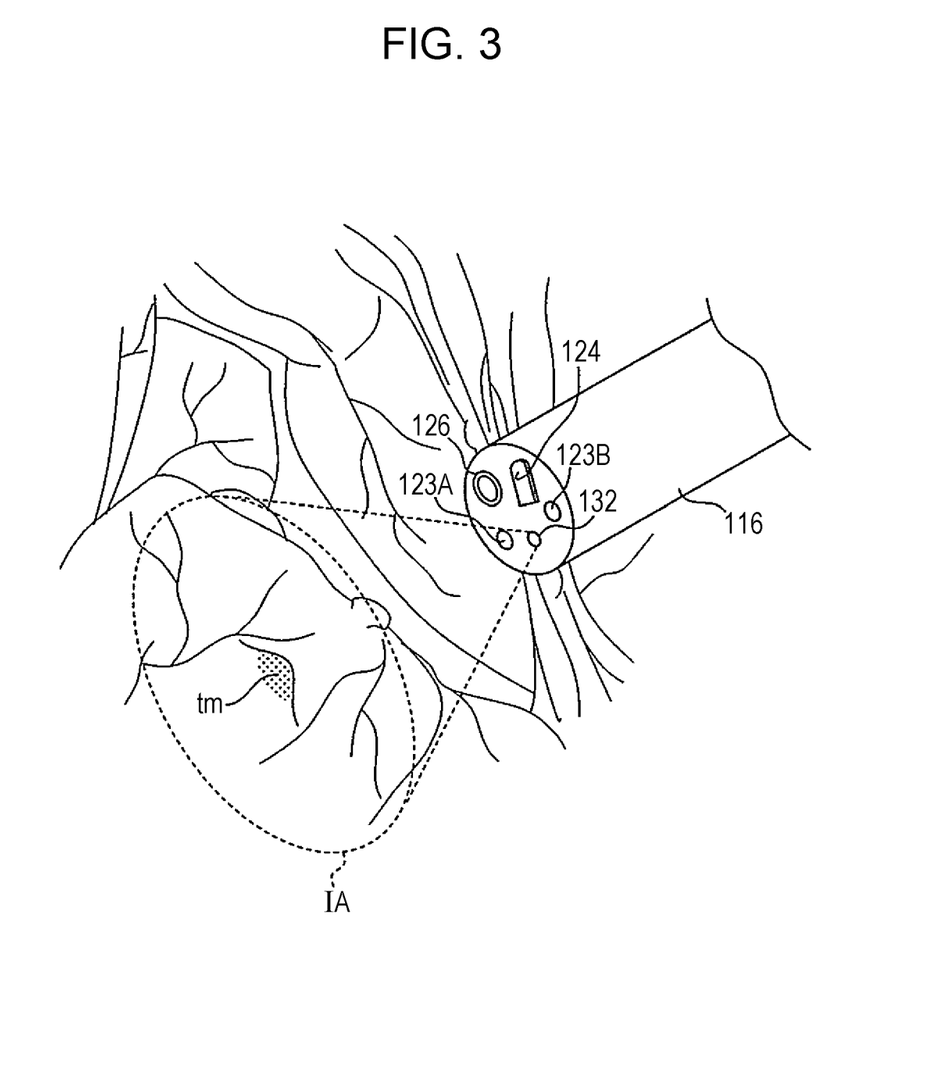
FIG. 3 is a diagram illustrating a state of observation using an endoscope included in the electronic apparatus system.

FIG. 3 is a diagram illustrating a state where the insertion section 104 of the endoscope apparatus 100 is inserted into a subject, and illustrating a state where an observation image is obtained via the imaging optical system 130. In FIG. 3, a reference symbol IA denotes an imaging range and a reference symbol tm denotes a tumor (a black raised portion in FIG. 3).

As illustrated in FIGS. 1 to 3, the illumination lens 123A (for visible light) and the illumination lens 123B (for infrared light) of the illumination unit 123 are disposed next to the lens 132 on the distal end surface of the distal end portion 116. An emission end of a light guide 170, which will be described below, is disposed behind the illumination lenses 123A and 123B. The light guide 170 is inserted through the insertion section 104, the handheld operation section 102, and a universal cable 106, and an incidence end of the light guide 170 is located in a light guide connector 108.

Configuration of Light Source Device

As illustrated in FIG. 2, the light source device 300 is constituted by a light source 310, a diaphragm 330, a condenser lens 340, and so forth, and causes illumination light to enter the light guide 170. The light source 310 includes a visible light source 310A and an infrared light source 310B and is capable of emitting one or both of visible light and infrared light. Accordingly, with the light guide connector 108 (see FIG. 1) being connected to the light source device 300, illumination light emitted by the light source device 300 is transmitted to the illumination lenses 123A and 123B through the light guide 170 and is applied to an observation range from the illumination lenses 123A and 123B.

Configuration of Endoscope Processor

Next, the configuration of the endoscope processor 200 will be described with reference to FIG. 2. In the endoscope processor 200, an image input controller 202 receives an image signal output from the endoscope apparatus 100, an image processing unit 204 performs necessary image processing thereon, and a video output unit 206 outputs a resulting image signal. Accordingly, an observation image is displayed on the monitor 400. These processes are performed under control of a central processing unit (CPU) 210. The image processing unit 204 performs, in addition to image processing such as white balance adjustment, switching or superimposition of an image displayed on the monitor 400, electronic zoom processing, display and switching of an image according to an operation mode, or extraction of a specific component (for example, a brightness signal) from an image signal.

The endoscope processor 200 includes the operation unit 208. The operation unit 208 includes an operation mode setting/selecting switch, a water supply instruction button, or the like (not illustrated), and is capable of performing an operation of emitting visible light or infrared light.

Configuration of Endoscope Operation Device

As illustrated in FIGS. 1 and 2, the endoscope operation device 500 (an apparatus operation device) includes a head-mounted terminal 510 (a pseudo display unit), a line-of-sight detecting camera 520 (a line-of-sight detecting unit), an arithmetic unit 530 (a line-of-sight detecting unit, a pseudo display unit, a gesture detecting unit, a determination unit, and a control unit), and a display 540 (a pseudo display unit).

The head-mounted terminal 510 is a terminal that is to be mounted on the head of a user and includes visual field cameras 512 and 514 (a pseudo display unit), each of which obtains a visual field image (an image obtained through photographing in a line-of-sight direction) of the user. The visual field cameras 512 and 514 are arranged so as to be located near the left and right eyes of the user when the head-mounted terminal 510 is mounted on the head of the user. With use of the visual field cameras 512 and 514, a stereo image is obtained, and then the arithmetic unit 530 calculates, based on the stereo image, the position of a photographic subject relative to the visual field cameras 512 and 514 and the distances from the visual field cameras 512 and 514 to the photographic subject. The line-of-sight detecting camera 520 is located near the monitor 400 and the display 540 and captures an image of an eye of the user. Accordingly, a line of sight of the user is detected. A plurality of line-of-sight detecting cameras 520 may be provided to reliably and stably detect a line of sight. The arithmetic unit 530 calculates, based on the stereo image obtained by the visual field cameras 512 and 514, the position of a photographic subject and the distance to the photographic subject; detects, based on an image of an eye captured by the line-of-sight detecting camera 520, a line of sight; controls pseudo display; detects a gesture performed on a virtual object; controls an operation of the endoscope apparatus 100; and so forth. The display 540 displays a visual field image and also displays a virtual object on the visual field image in a pseudo manner.

The details of the operation of the endoscope apparatus 100 performed by the endoscope operation device 500 having the above-described configuration will be described below.

Usage Situation of Endoscope Operation Device

Figure 4:
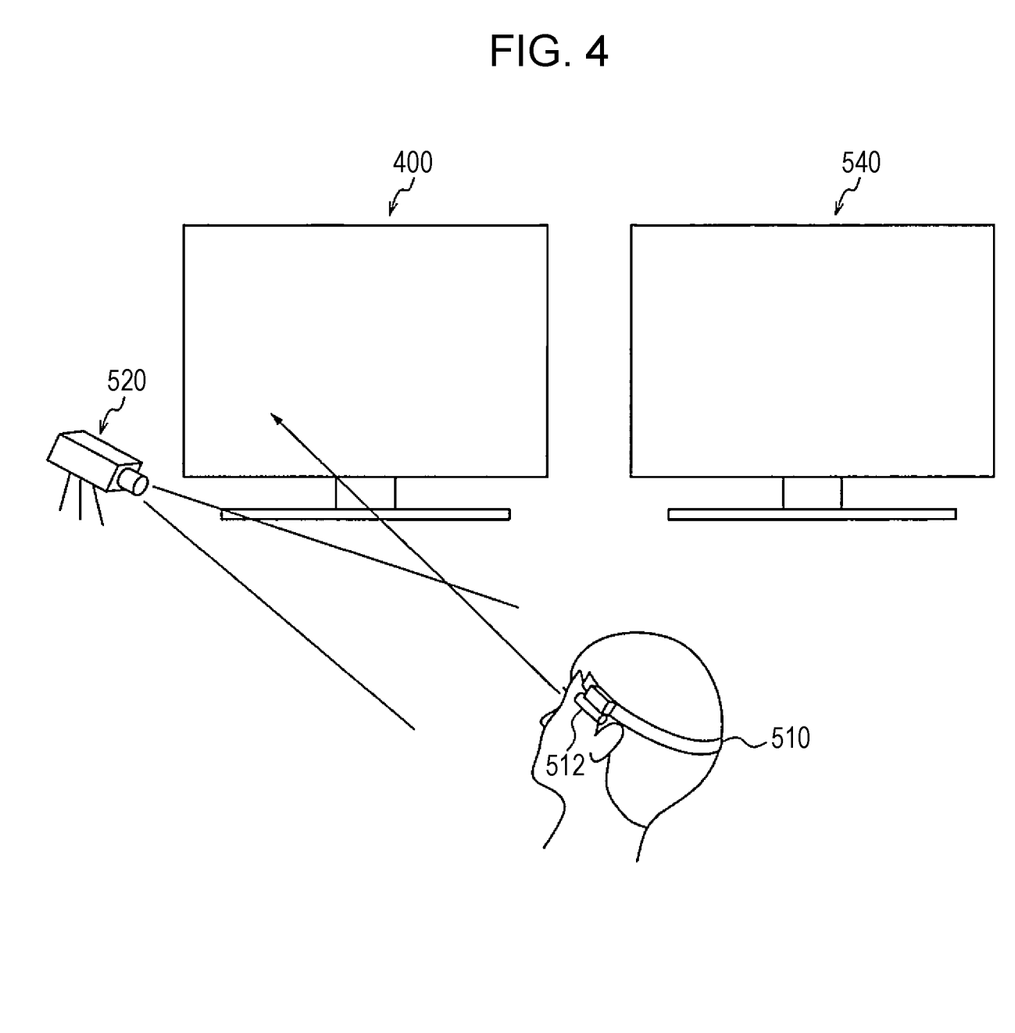
FIG. 4 is a diagram illustrating a state where the electronic apparatus system is being used.

FIG. 4 is a conceptual diagram illustrating a state where the endoscope apparatus 100 is operated by using the endoscope operation device 500. In the example illustrated in FIG. 4, a user who is wearing the head-mounted terminal 510 is looking at the monitor 400 and the display 540 while operating the endoscope apparatus 100, and the visual field cameras 512 and 514 are continuously obtaining visual field images of the user (the visual field camera 514 is not illustrated here). The line-of-sight detecting camera 520 is provided near the monitor 400 and the display 540 and obtains an image of the eyes of the user.

Operation of Endoscope Apparatus Using Endoscope Operation Device

Figure 5:
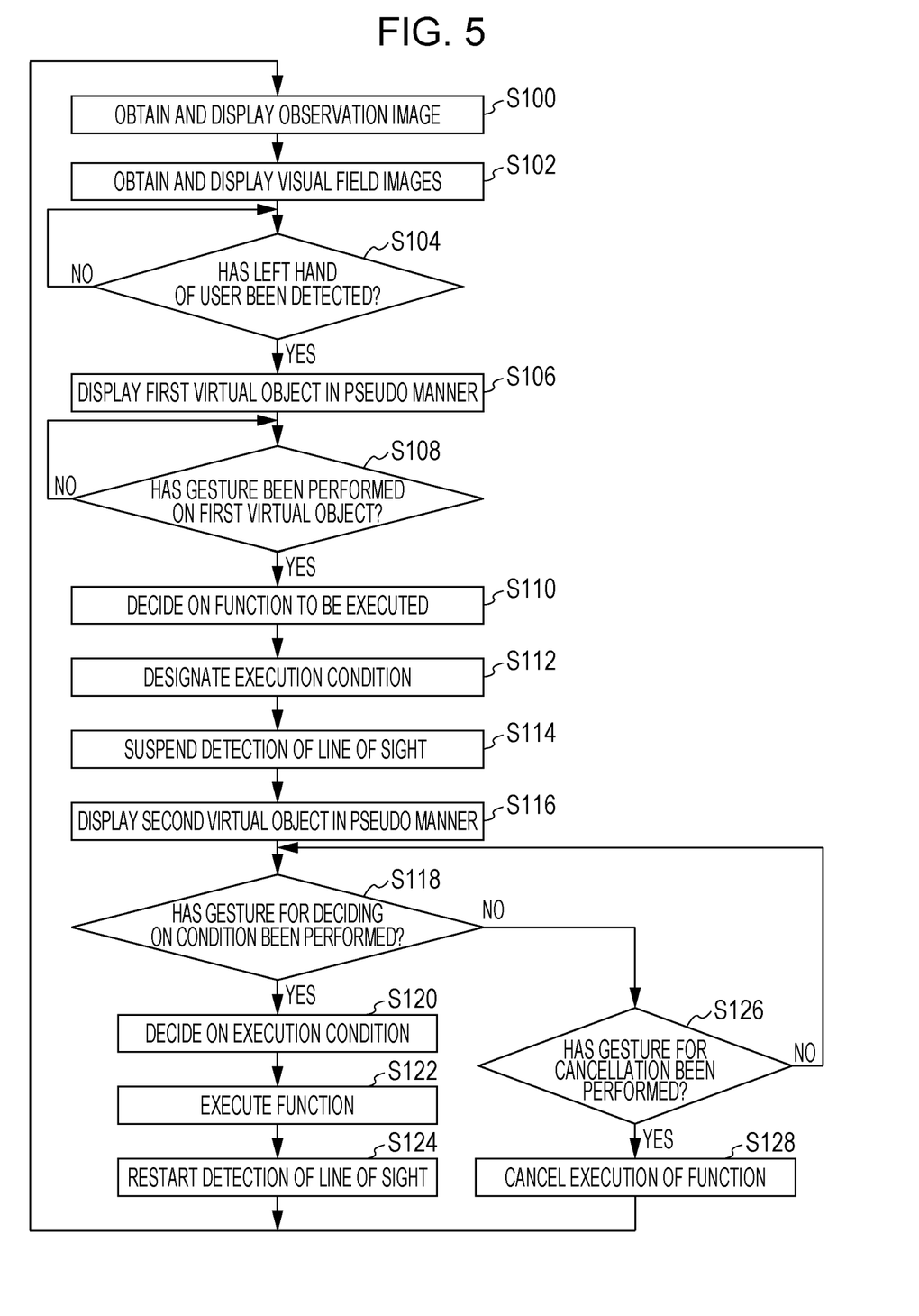
FIG. 5 is a flowchart illustrating a process of operating an apparatus in the electronic apparatus system according to an embodiment of the present invention.

Next, a description will be given of an operation of the endoscope apparatus 100 performed by using the endoscope operation device 500 in the endoscope system 10 having the above-described configuration. FIG. 5 is a flowchart illustrating an operation process of the endoscope apparatus 100. The flowchart in FIG. 5 illustrates a process in a case where the endoscope operation device 500 operates the endoscope apparatus 100 to process an observation image displayed on the monitor 400.

Figure 6:
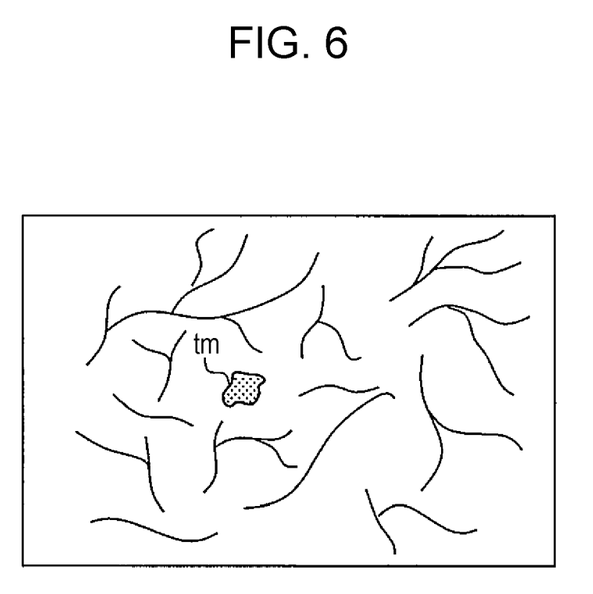
FIG. 6 is a diagram illustrating an example of an image obtained by the endoscope.

Upon the process being started, in step S100, an observation image is obtained via the imaging optical system 130 of the endoscope apparatus 100 as illustrated in FIG. 3 and the observation image is displayed on the monitor 400 as illustrated in FIG. 6 (a reference symbol tm in FIG. 6 denotes a tumor, as in FIG. 3). Subsequently, the process proceeds to step S102, where visual field images of a user captured by the visual field cameras 512 and 514 are obtained.

Figure 7A:
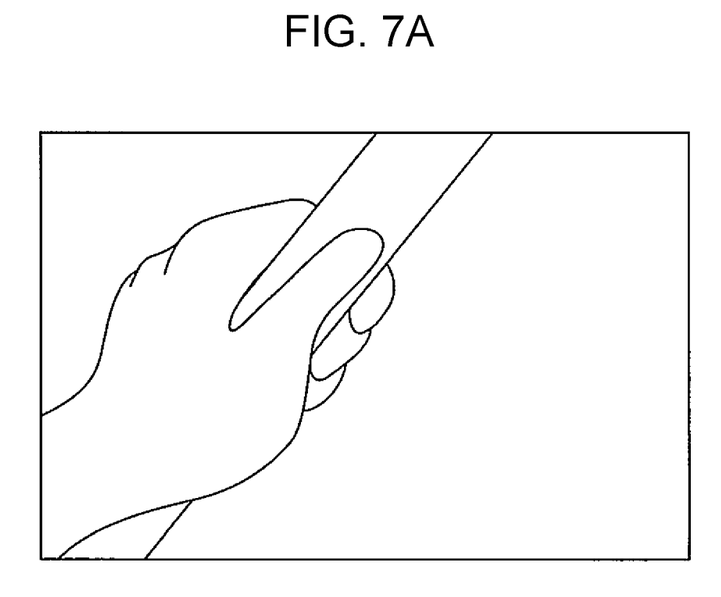
FIGS. 7A and 7B are diagrams illustrating a state where virtual objects are displayed in a pseudo manner.

In this embodiment, a virtual object is displayed on the display 540 in a pseudo manner, as will be described in detail below. A condition for starting pseudo display is satisfied when a specific object is recognized in a visual field image. Specifically, as illustrated in FIG. 7A, it is determined whether or not a hand (left hand) of the user has been recognized in a visual field image (step S104). If the left hand is detected (YES in step S104), the process proceeds to step S106 and pseudo display is started. The determination in step S104 is repeated until the left hand is detected.

Figure 7B:
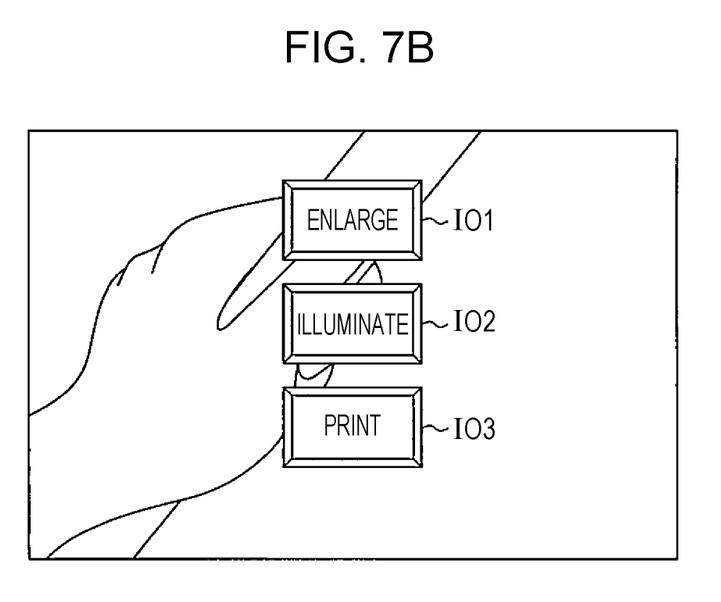

In step S106, virtual objects corresponding to functions that can be executed when the hand is recognized among functions of the endoscope apparatus 100 are displayed in a pseudo manner at the position of the hand of the user in the image displayed on the display 540, as illustrated in FIG. 7B. The position of the hand in the pseudo display can be calculated based on a stereo image obtained by the visual field cameras 512 and 514, as described above. In this embodiment, a description is given of a case where an observation image of the endoscope apparatus 100 is displayed on the monitor 400 (see FIG. 6), and enlargement, printing, and illumination (change of illumination) can be performed on the observation image. As illustrated in FIG. 7B, virtual objects IO1, IO2, and IO3 (a first virtual object), which are keys of a keyboard on which characters representing individual functions are written, are displayed in a pseudo manner. As will be described in detail below, these virtual objects IO1, IO2, and IO3 can be operated in a pseudo manner by gesture.

In the recognition of a hand and the pseudo display in steps S104 and S106, a real object or space, not a figure or the like (marker) of a predetermined pattern, is recognized by using a vision-based markerless augmented reality (AR) technology, and a virtual object is displayed at the position of and near the recognized object or the like. Pseudo display can be performed even if there is no marker, and thus restrictions on the arrangement of an apparatus can be reduced. Note that, in the present invention, pseudo display is not limited to that performed by using the markerless AR technology. Pseudo display may be performed by using a marker-based AR technology in accordance with a condition, such as restrictions on the arrangement of an apparatus. The AR technologies are introduced in, for example, the following website.

http://www.atmarkit.co.jp/ait/articles/1109/26/news136_2.html

In this embodiment, the left hand of the user is recognized and displayed in a pseudo manner. The object to be recognized is not limited to the left hand, but may be another part of the body, such as the right hand or a foot, or may be an object other than the body of the user. For example, the handheld operation section 102 of the endoscope apparatus 100 may be recognized and displayed in a pseudo manner. In the case of using the marker-based AR technology, a marker may be provided to the hand or glove of the user or the handheld operation section 102 by attaching the marker thereto.

After the virtual objects IO1, IO2, and IO3 are displayed in step S106, the process proceeds to step S108, where it is determined whether or not a gesture (a first gesture) has been performed on the virtual object IO1, IO2, or IO3. Specifically, it is determined in the following steps 1 to 4 whether or not a gesture of touching or pressing any one of the virtual objects IO1, IO2, and IO3 has been performed. Here, it is assumed that the user touches any one of the virtual objects IO1, IO2, and IO3 with a finger of the right hand. At this time, a message indicating a gesture to be performed on the virtual object IO1, IO2, or IO3 (for example, "touch the key to be executed with the right hand") may be displayed on the screen of the display 540.

(Step 1) A stereo image of the vicinity of the left hand of the user is obtained by the visual field cameras 512 and 514.

(Step 2) Based on the obtained stereo image, the positional relationship between a finger of the right hand and the virtual objects IO1, IO2, and IO3 that are displayed in a pseudo manner is calculated by the arithmetic unit 530.

(Step 3) If the user moves the hand and if the distance between any one of the virtual objects IO1, IO2, and IO3 and the finger of the right hand becomes smaller than or equal to a threshold, it is determined that a gesture of touching the virtual object has been performed. The distance can be calculated based on the stereo image obtained by the visual field cameras 512 and 514.

Figure 8A:
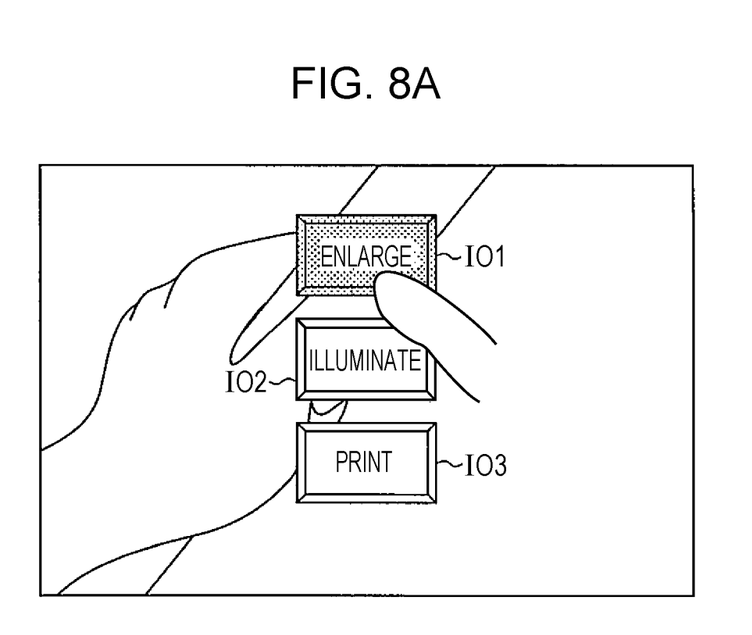
FIGS. 8A and 8B are diagrams illustrating a gesture performed on a virtual object that is displayed in a pseudo manner.

(Step 4) If it is determined that a gesture has been performed, the color of the virtual object as a target of the gesture is changed, thereby notifying the user that the gesture has been detected. FIG. 8A illustrates an example of a case where a gesture is performed on the virtual object IO1 and the color of the virtual object IO1 is changed accordingly. In addition to changing the color or instead of changing the color, the shape of the virtual object IO1 may be changed.

If it is determined in step S108 that a gesture has been performed, the function corresponding to the virtual object as a target of the gesture is determined on as the function to be executed by the endoscope apparatus 100, which is a target apparatus to be operated (step S110: determination step). In this embodiment, it is determined that a gesture has been performed on the virtual object IO1, as illustrated in FIG. 8A, and the observation image displayed on the monitor 400 is enlarged.

Figure 9A:
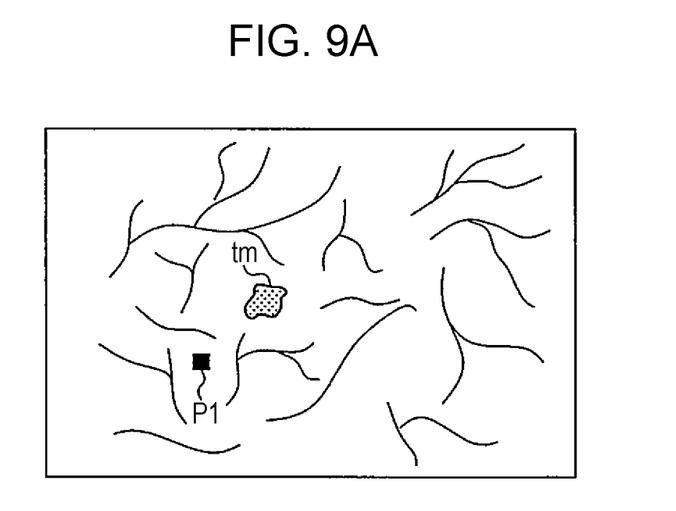
FIGS. 9A and 9B are diagrams illustrating a state where an enlargement range of an image is designated by using a line of sight.
Figure 9B:
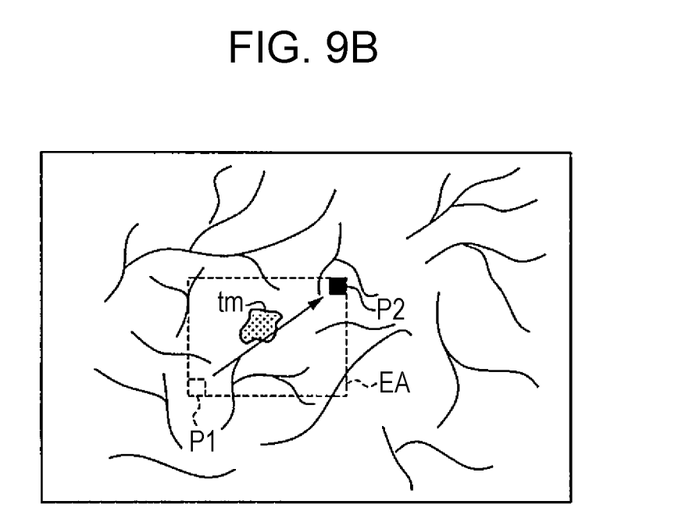

An execution condition for a function to be executed by the endoscope apparatus 100 (here, an enlargement range, which is an execution condition for a function of enlarging an image) can be designated by using a line of sight (step S112). Specifically, a point of gaze P1 (FIG. 9A) is detected from an image of an eye of the user obtained by the line-of-sight detecting camera 520, and then a point of gaze P2 (FIG. 9B) is detected in accordance with a movement of a line of sight of the user. A rectangular region EA, in which the point of gaze P1 and the point of gaze P2 are at the lower left corner and the upper right corner, respectively, is regarded as an enlargement range. At this time, since the direction of a line of sight is unstable, a point that has been gazed at for a predetermined period of time (for example, 3 seconds) or more may be detected as a point of gaze.

A line of sight (point of gaze) can be detected from an image of an eye of the user, based on the position of the iris, which is a movable point (movable portion), relative to the inner corner of the eye, which is a reference point (unmovable portion). In this case, for example, when the iris of the left eye is far from the inner corner of the left eye, the user is looking left. On the other hand, when the iris of the left eye is close to the inner corner of the left eye, the user is looking right.

A line of sight can also be detected based on the position of the pupil, which is a movable point, relative to the position of the corneal reflection, which is a reference point. In this case, for example, when the pupil of the left eye is closer than the corneal reflection to the outer corner side of the left eye, the user is looking left. When the pupil of the left eye is closer than the corneal reflection to the inner corner side of the left eye, the user is looking right. In the case of using this method, the face of the user is irradiated with infrared rays and photographed by an infrared camera.

The above-described technique for detecting a line of sight is introduced in, for example, the following website. http://jp.fujitsu.com/group/labs/techinfo/techguide/list/eye-movements_p03.html After the enlargement range is set in step S112, the process proceeds to step S114, where the process of detecting a line of sight is suspended, and the process proceeds to step S116. The process of detecting a line of sight is suspended in step S114 to fix the set enlargement range so that the enlargement range is not changed because a line of sight (point of gaze) is likely to move unstably. After the execution condition for enlarging an image has been decided on, the suspension of detection of a line of sight is cancelled (detection of a line of sight is restarted) in step S124.

Figure 8B:
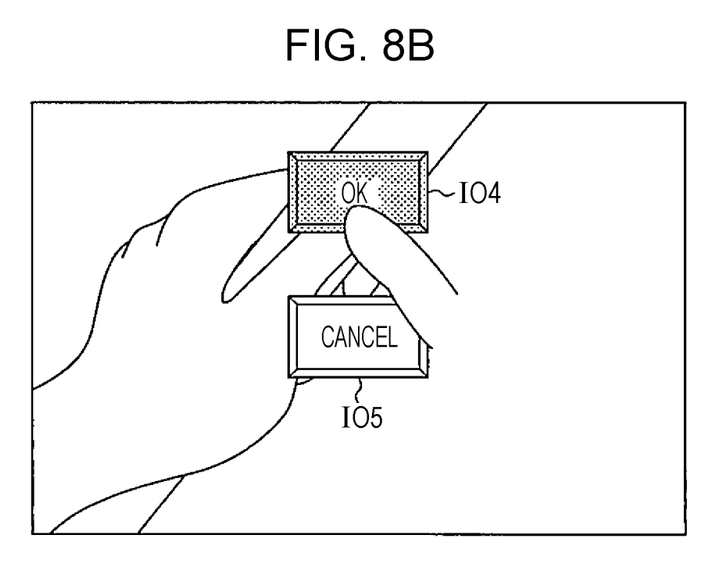

In step S116, virtual objects IO4 and IO5 (a second virtual object) for deciding on the image enlargement range or cancelling image enlargement are displayed on the display 540 in a pseudo manner (see FIG. 8B). The virtual objects IO4 and IO5 are virtual objects imitating an OK button and a cancel button, respectively.

After the virtual objects IO4 and IO5 are displayed, the process proceeds to step S118 (determination step), where it is determined whether or not a gesture (a second gesture) has been performed on either of the virtual objects IO4 and IO5. This gesture is a gesture of touching or pressing a button with a finger of the right hand, as in step S108. Whether or not a gesture has been performed can be determined based on a stereo image captured by the visual field cameras 512 and 514, as in steps S104 and S108.

If a gesture performed on the virtual object IO4 is detected (YES in step S118), the process proceeds to step S120 (a determination step), where the execution condition for image enlargement (the enlargement range: region EA in FIG. 9B) is decided on, and the process proceeds to step S122. On the other hand, if a gesture performed on the virtual object IO5 is detected (NO in step S118, YES in step S126), image enlargement is cancelled (step S128) and the process returns to step S100. Upon a gesture performed on either of the virtual objects IO4 or IO5 being detected, detection of a gesture is finished.

Figure 10:
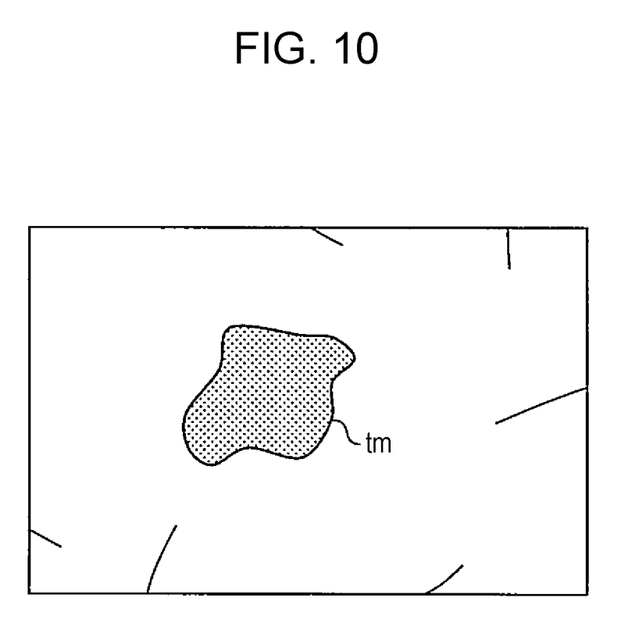
FIG. 10 is a diagram illustrating an enlarged image.

In step S122 (a control step), the function of the endoscope apparatus 100 is executed in accordance with the execution condition designated in step S120. Specifically, the arithmetic unit 530 instructs the endoscope processor 200 to enlarge and display the range of the region EA, and the endoscope processor 200 enlarges the range of the region EA by using the image processing unit 204 and causes the monitor 400 to display the enlarged image (see FIG. 10). After the enlarged image is displayed, the process proceeds to step S124, where the suspension of detection of a line of sight is cancelled, and the process returns to step S100.

As described above, with use of the endoscope system 10 according to this embodiment, it is not necessary to touch an actual keyboard, mouse, or button to operate the endoscope apparatus 100 (to enlarge an image in the foregoing example), and thus it is not necessary to shift an instrument from one hand to the other hand or peel of/put on gloves in a medical setting. Accordingly, a necessary operation can be easily performed by using a line of sight and a gesture (for example, a gesture with the right hand). In addition, it is not necessary to provide a keyboard, mouse, or button for operating the endoscope apparatus 100, and restrictions on the arrangement of the apparatus can be reduced. Furthermore, virtual objects corresponding to an apparatus to be operated and operation details are displayed in a pseudo manner (in the foregoing example, characters representing executable functions are displayed on virtual keys), and thus the virtual object on which an operation is to be performed can be easily determined.

In the endoscope system 10, the operation details of the endoscope apparatus 100 are not limited to the foregoing examples, such as display with enlargement, change of illumination, and printing. Another function of the endoscope apparatus 100 may be executed. The virtual objects that are displayed in a pseudo manner are not limited to keys or buttons, but may be dials, levers, switches, or the like. The virtual objects may be displayed by superimposing them on an observation image on the monitor 400 or may be displayed in a switched manner.

A gesture for operating the endoscope apparatus 100 is not limited to pressing of a key or a button, but may be set in accordance with a virtual object. For example, an action of rotating a dial, moving a lever, or grasping a grip may be performed. A gesture is not limited to an action of moving a finger of a hand, but may be an action of moving a fingertip, wrist, or foot.

According to the one aspect, a gesture is detected by associating the first and second virtual objects with the first and second gestures, respectively, and thus a target to be operated and operation details can be designated reliably and easily.

According to the one aspect, a function to be executed by a target apparatus to be operated and an execution condition can be designated, and thus the user can easily perform an intended operation.

According to the one aspect, conditions for starting and finishing detection of a line of sight are provided, so that detection of a line of sight, operation of an apparatus, and so forth can be stably performed.

According to the one aspect, the medical apparatus may be an endoscope apparatus, an X-ray diagnostic apparatus, an ultrasound diagnostic apparatus, an image interpretation support apparatus, a dental diagnostic/treatment apparatus, or the like, but is not limited thereto.

Others

In the foregoing embodiment, a description has been given of a case where the target apparatus to be operated is the endoscope apparatus 100, which is a medical apparatus. However, the target apparatus to be operated in the present invention is not necessarily a medical apparatus. The embodiment is applicable to an operation of a mobile apparatus, such as a smartphone, a tablet terminal, or a game machine, as well as a medical apparatus, and to an operation of an apparatus under a situation where it is impossible to freely use both hands while operating an apparatus, for example, driving a car, or a situation where the arrangement of an apparatus is restricted. A necessary operation can be easily performed by using a line of sight and a gesture performed on a virtual object, and restrictions on the arrangement of the apparatus can be reduced. The target apparatus to be operated is not limited to a single apparatus. One of a plurality of apparatuses may be selected by using a line of sight and a gesture. In the present invention, a gesture may be performed by using both hands, not one of the hands, depending on the target apparatus to be operated, the usage situation of the apparatus, the type or importance of an operation, or the like. A user as a target of line-of-sight detection and a user as a target of gesture detection may be different from each other.

REFERENCE SIGNS LIST

10 endoscope system
100 endoscope apparatus
110 endoscope main body
200 endoscope processor
300 light source device
400 monitor
500 endoscope operation device
510 head-mounted terminal
512, 514 visual field camera
520 line-of-sight detecting camera
530 arithmetic unit
540 display
IO1, IO2, IO3, IO4, IO5 virtual object
P1, P2 point of gaze

What is claimed is:

1. An apparatus operation device comprising:
    a display that displays a virtual object in a pseudo manner; and
    a processor configured to:
        detect a line of sight of a user,
        detect one or more gestures of the user performed on the virtual object that is displayed in a pseudo manner,
        determine, based on the line of sight that has been detected and the one or more gestures that have been detected, a target apparatus to be operated and operation details for the target apparatus,
        control the target apparatus and causes the target apparatus to execute the operation details that have been determined,
        detect a first point of gaze from an image of the user's eye, and detect a second point of gaze according to a movement of the line of sight,
        determine, based on the movement of the line of sight between the detected first point of gaze and second point of gaze, the target apparatus and the operation details for the target apparatus, and
        determine an operation target region in which the first point of gaze and second point of gaze are on a border.

2. The apparatus operation device according to claim 1, wherein the processor is further configured to:
    determine, based on the movement of the line of sight that has been detected and a first gesture among the one or more gestures that have been detected, the target apparatus and the operation details, and
    confirm the determination, based on a second gesture among the one or more gestures that have been detected.

3. The apparatus operation device according to claim 2, wherein
    the virtual object is one of a plurality of virtual objects,
    the display displays the plurality of virtual objects in a pseudo manner, and
    the processor is further configured to detect, as the first gesture, a gesture performed on a first virtual object among the plurality virtual objects, and detects, as the second gesture, a gesture performed on a second virtual object among the plurality of virtual objects.

4. The apparatus operation device according claim 1, wherein the operation details include a function that the processor causes the target apparatus to execute, and an execution condition for the function.

5. The apparatus operation device according claim 2, wherein the operation details include a function that the processor causes the target apparatus to execute, and an execution condition for the function.

6. The apparatus operation device according claim 3, wherein the operation details include a function that the processor causes the target apparatus to execute, and an execution condition for the function.

7. The apparatus operation device according to claim 1, wherein the processor is further configured to detect a hand gesture of the user.

8. The apparatus operation device according to claim 2, wherein the processor is further configured to detect a hand gesture of the user.

9. The apparatus operation device according to claim 3, wherein the processor is further configured to detect a hand gesture of the user.

10. The apparatus operation device according to claim 4, wherein the processor is further configured to detect a hand gesture of the user.

11. The apparatus operation device according to claim 5, wherein the processor is further configured to detect a hand gesture of the user.

12. The apparatus operation device according to claim 6, wherein the processor is further configured to detect a hand gesture of the user.

13. The apparatus operation device according to claim 1, wherein the processor is further configured to suspend detection of the line of sight upon detection of the one or more gestures being started, and start detection of the line of sight upon detection of the one or more gestures being finished.

14. The apparatus operation device according to claim 2, wherein the processor is further configured to suspend detection of the line of sight upon detection of the one or more gestures being started, and start detection of the line of sight upon detection of the one or more gestures being finished.

15. The apparatus operation device according to claim 3, wherein the processor is further configured to suspend detection of the line of sight upon detection of the one or more gestures being started, and start detection of the line of sight upon detection of the one or more gestures being finished.

16. The apparatus operation device according to claim 4, wherein the processor is further configured to suspend detection of the line of sight upon detection of the one or more gestures being started, and start detection of the line of sight upon detection of the one or more gestures being finished.

17. An apparatus operation method for an apparatus operation device comprising a line-of-sight detecting camera that detect a first point of gaze from an image of the user's eye, and a second point of gaze according to a movement of the line of sight, a display that displays a virtual object in a pseudo manner, and a processor configured to detect one or more gestures of the user performed on the virtual object that is displayed in a pseudo manner, the apparatus operation method comprising:

a determination step of determining, based on the line of sight between the first point of gaze and the second point of gaze that has been detected and the one or more gestures that have been detected, a target apparatus to be operated and operation details for the target apparatus, and determining an operation target region in which the first point of gaze and second point of gaze are on a border; and a control step of controlling the target apparatus and causing the target apparatus to execute the operation details that have been determined.

18. An electronic apparatus system comprising:
the apparatus operation device according to claim 1; and
an electronic apparatus which is the target apparatus.

19. The electronic apparatus system according to claim 18, wherein
the electronic apparatus comprises an image display unit that displays an image, and
the processor is further configured to control the electronic apparatus and causes the electronic apparatus to process the image displayed on the image display unit.

20. The electronic apparatus system according to claim 18, wherein the electronic apparatus is a medical apparatus.

21. The apparatus operation device according to claim 1, wherein the display displays a visual field image of the user and a virtual object on the visual field image in the pseudo manner.

22. The apparatus operation device according to claim 21, wherein
the processor further configured to detect a hand of a user in a visual field image of the user, and
the display displays the virtual object at a position of the hand in the visual field image in the pseudo manner.

23. An endoscope system comprising:
the apparatus operation device according to claim 1;
an endoscope apparatus that is the target apparatus; and
an endoscope operation device that controls the endoscope apparatus.

* * * * *